(12) United States Patent
Hamidzai et al.

(10) Patent No.: US 10,946,321 B1
(45) Date of Patent: Mar. 16, 2021

(54) UV ENABLED FINS ENCAPSULATION SYSTEM

(71) Applicants: Ilyas Hamidzai, Bethesda, MD (US); Gary Steven Davidson, Bethesda, MD (US); Nackieb Mohd Kamin, Annandale, VA (US)

(72) Inventors: Ilyas Hamidzai, Bethesda, MD (US); Gary Steven Davidson, Bethesda, MD (US); Nackieb Mohd Kamin, Annandale, VA (US)

(73) Assignee: UV American Technology, LLC, Bethesda, MD (US)

( * ) Notice: Subject to any disclaimer, the term of this patent is extended or adjusted under 35 U.S.C. 154(b) by 0 days.

(21) Appl. No.: 16/988,114

(22) Filed: Aug. 7, 2020

(51) Int. Cl.
| A61L 9/20 | (2006.01) |
| B01D 46/00 | (2006.01) |
| B01D 46/42 | (2006.01) |
| B01D 46/44 | (2006.01) |

(52) U.S. Cl.
CPC ............ *B01D 46/0028* (2013.01); *A61L 9/20* (2013.01); *B01D 46/0005* (2013.01); *B01D 46/0086* (2013.01); *B01D 46/0091* (2013.01); *B01D 46/4245* (2013.01); *B01D 46/442* (2013.01); *B01D 46/448* (2013.01); *A61L 2209/111* (2013.01); *A61L 2209/12* (2013.01); *A61L 2209/14* (2013.01); *A61L 2209/15* (2013.01)

(58) Field of Classification Search
CPC ............ B01D 46/0028; B01D 46/0005; B01D 46/4245; B01D 46/442; B01D 46/0086; A61L 9/20; A61L 2209/15; A61L 2209/14; A61L 2209/111
USPC ........ 55/385.2, 484, 489, DIG. 31, DIG. 34; 96/397; 422/24, 121, 186.07
See application file for complete search history.

(56) References Cited

U.S. PATENT DOCUMENTS

| 4,792,345 | A | * | 12/1988 | Abe | ...................... F24F 3/1603 96/397 |
| 5,837,207 | A | * | 11/1998 | Summers | .................. A61L 9/20 422/121 |
| 6,132,784 | A | | 10/2000 | Brandt et al. | |
| 6,500,387 | B1 | * | 12/2002 | Bigelow | ................... A61L 9/20 250/432 R |
| 6,849,107 | B1 | | 2/2005 | Huffman | |
| 9,039,966 | B2 | | 5/2015 | Anderson et al. | |
| 9,518,487 | B2 | * | 12/2016 | Coelho Ferreira | .... B01D 46/50 |
| 9,587,846 | B2 | * | 3/2017 | Dobbyn | ............ B01D 46/0086 |
| 9,937,453 | B2 | * | 4/2018 | Baek | ...................... F24F 3/1603 |
| 10,357,582 | B1 | | 7/2019 | Barron et al. | |
| 10,363,325 | B2 | | 7/2019 | Hawkins et al. | |
| 10,413,626 | B1 | | 9/2019 | Barron et al. | |
| 2004/0146437 | A1 | * | 7/2004 | Arts | ........................ A61L 9/015 422/186.07 |
| 2007/0220851 | A1 | * | 9/2007 | Parker | ....................... F24F 3/16 55/484 |

(Continued)

*Primary Examiner* — Minh Chau T Pham
(74) *Attorney, Agent, or Firm* — Nixon & Vanderhye PC

(57) ABSTRACT

A general-purpose air sterilizing system destroys activation of air-borne pathogens, designed with different embodiments. The methods used to build the apparatus allows destroying airborne pathogens like bacteria, mold, mildew, allergens and deactivates viruses such as SARS CoV-2. The apparatus supports air circulation system that contains filter which comprising array of Ultraviolet (UV) Light Emitting Diode (LEDs) of 262-nm wavelength, AKA UVC, are used.

21 Claims, 20 Drawing Sheets

(56) References Cited

U.S. PATENT DOCUMENTS

| | | | |
|---|---|---|---|
| 2008/0310996 A1* | 12/2008 | Kim | A61L 9/20 422/24 |
| 2014/0223873 A1* | 8/2014 | Ebrahimi Warkiani | B01D 67/0062 55/489 |
| 2016/0184467 A1* | 6/2016 | Cheng | A61L 2/10 422/24 |
| 2017/0348445 A1* | 12/2017 | Bogdanovich | A61L 2/10 |
| 2019/0015541 A1* | 1/2019 | Peczalski | A61M 16/0616 |

* cited by examiner

UV ENABLED FINS ENCAPSULATION SYSTEM

CROSS-REFERENCES TO RELATED APPLICATIONS

None.

STATEMENT REGARDING FEDERALLY SPONSORED RESEARCH OR DEVELOPMENT

None.

BACKGROUND & SUMMARY

Recent increase in outbreak of severe airborne viral infectious diseases that attack respiratory systems caused by viruses have led to epidemic and pandemic spread with little to no immunity. In particular, Severe Acute Respiratory Syndrome Coronavirus 2 (SARS COV-2), was declared as pandemic in late 2019. The single-strand enveloped RNA virus belongs to the family of Coronaviridae, SARS COV-2 is unlikely virus to disappear but become part of the repertoire of repertory viruses that infect humans regularly.

Besides continuous use of Personal Protection Equipment (PPE), sanitizing air circulation systems is recommended by healthcare professionals as prevention measures of infectious diseases.

Technology herein provides effective methods and techniques to eliminate activation of air-borne pathogens prior to entering or recirculating through an air circulation system.

An example non-limiting system provides sterilization to deactivate airborne pathogens, on the surface of a conventional filter and in the air intake and outlet.

DETAILED DESCRIPTION OF EXAMPLE NON-LIMITING EMBODIMENTS

An example non-limiting system provides sterilization to deactivate airborne pathogens, on the surface of a conventional air filter and in the air intake and outlet.

An example design includes an air filter frame, uniquely designed ultraviolet (UV) light emitting diode (LEDs) disinfection arrays and a power module. The air sterilizing system uses a novel frame design that encapsulates any size air filter and the novel frame integration design of arrayed UVC LEDs. The system provides utility of air cleaning chamber, adapted to support HVAC filters. The system employs a unique array of UVC lamps in an intake chamber and return Air Duct (filter side 1) and on an outlet side of chamber (filter side 2).

Each air cleaning apparatus includes sterilization UV light exposing intake air, outlet and air filter surface area where air is drawn through a filter that is irradiated with a UVC array comprised of a UV germicidal air disinfection system. The mechanism eliminates pathogens such as bacteria, mold, mildew allergens, and deactivates viruses such as SARS CoV-2, The system also keeps a user up to date on air quality, functionality and effectiveness of the system.

The technology herein further provides an effective method to eliminate activation of airborne pathogens prior to entering the air circulation system.

In more detail, one embodiment provides an air filter encapsulation with integrated sensors using UVC LEDs emitting at wavelength of 200-280-nanometers range to sterilize and deactivate airborne pathogens, on the surfaces of a conventional filter and in an air intake and outlet. Each design includes an air filter frame, uniquely designed ultraviolet (UV) light emitting diode (LEDs) disinfection arrays and a power module. The air sterilizing system uses novel frame design that encapsulates any size air filter and the novel frame integration design of arrayed UVC LEDs. The claims are based on utility of air cleaning encapsulation, adapted to support HVAC filters. The system employs a unique array of UVC lamps in intake chamber and return Air Duct (filter side 1) and on an outlet side of chamber (filter side 2).

A power control module provides controlled energy to UVC arrays to illuminate UV light at a given power; and power to sensors for detecting air quality, carbon monoxide, and other safety parameters.

A WiFi enabled mobile app monitors the output of the sensors to user including cautioning user of unusual conditions of the system, indicative of failures or unsafe levels of air quality.

Example Air Filter Encapsulation System

Figure 1:
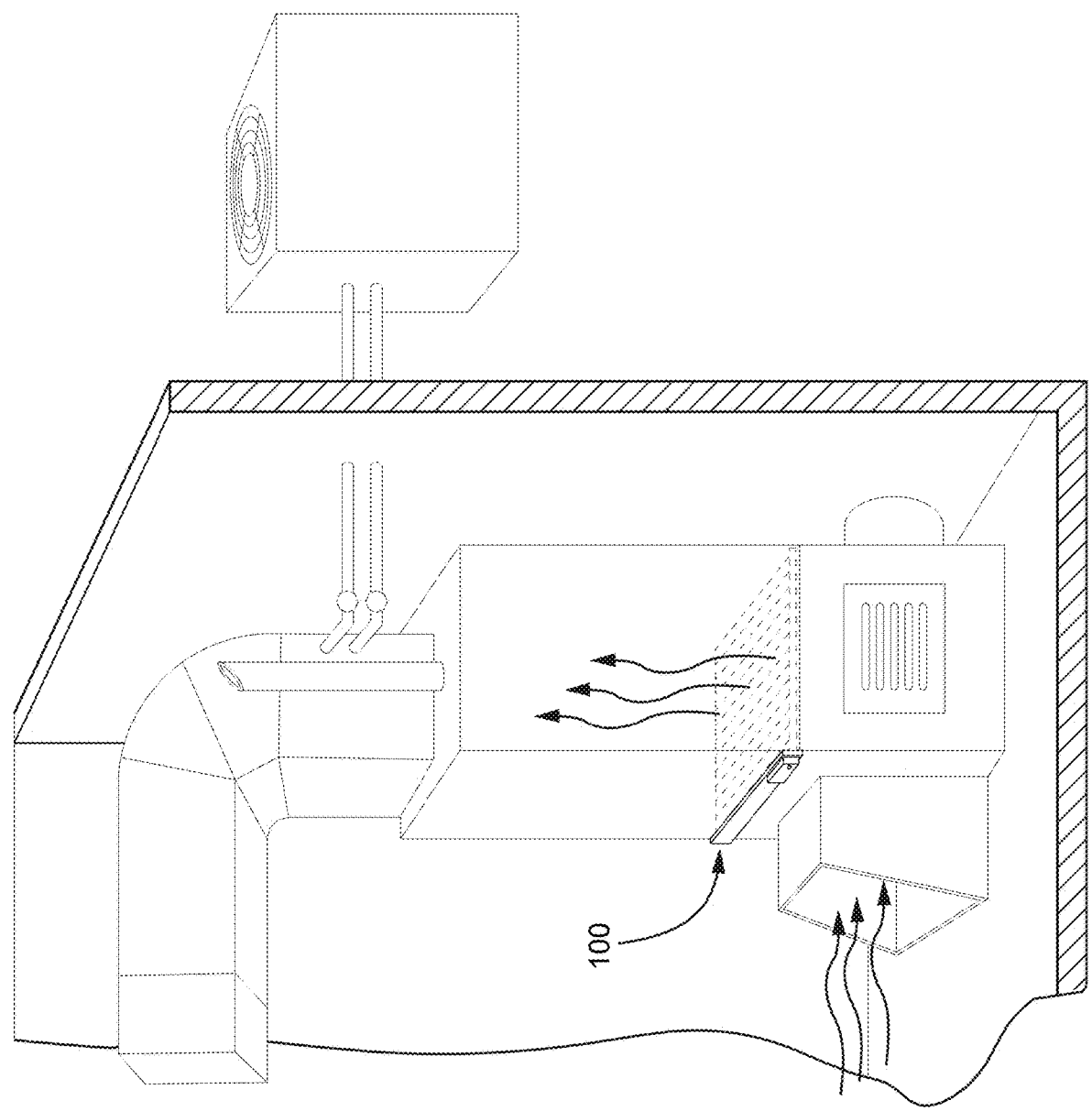
FIG. 1 shows an example non-limiting embodiment of an air handler/recirculation system including an encapsulated air filter.
Figure 2A:
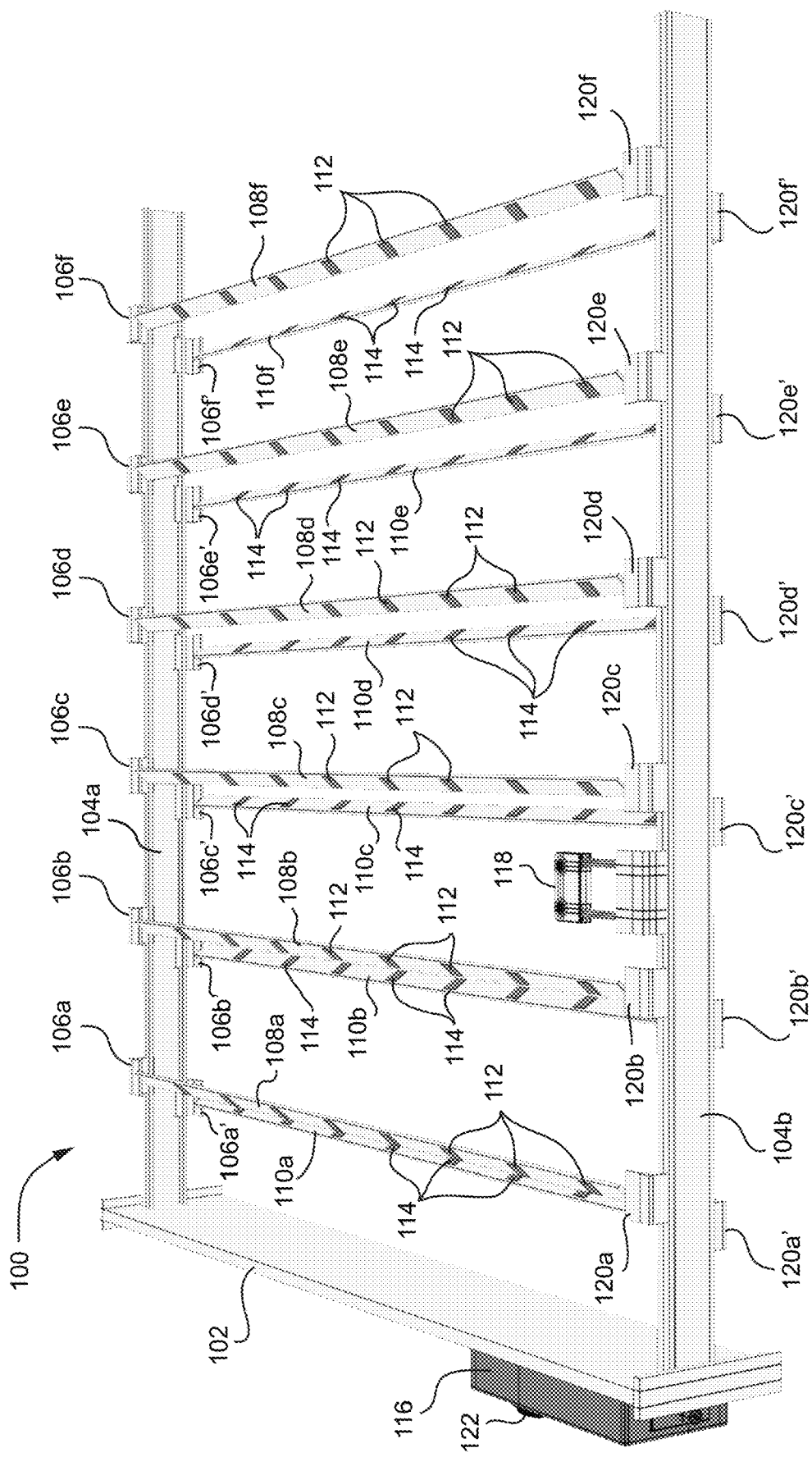
FIG. 2A is a side elevated view of an example non-limiting air filter frame structure.
Figure 2B:
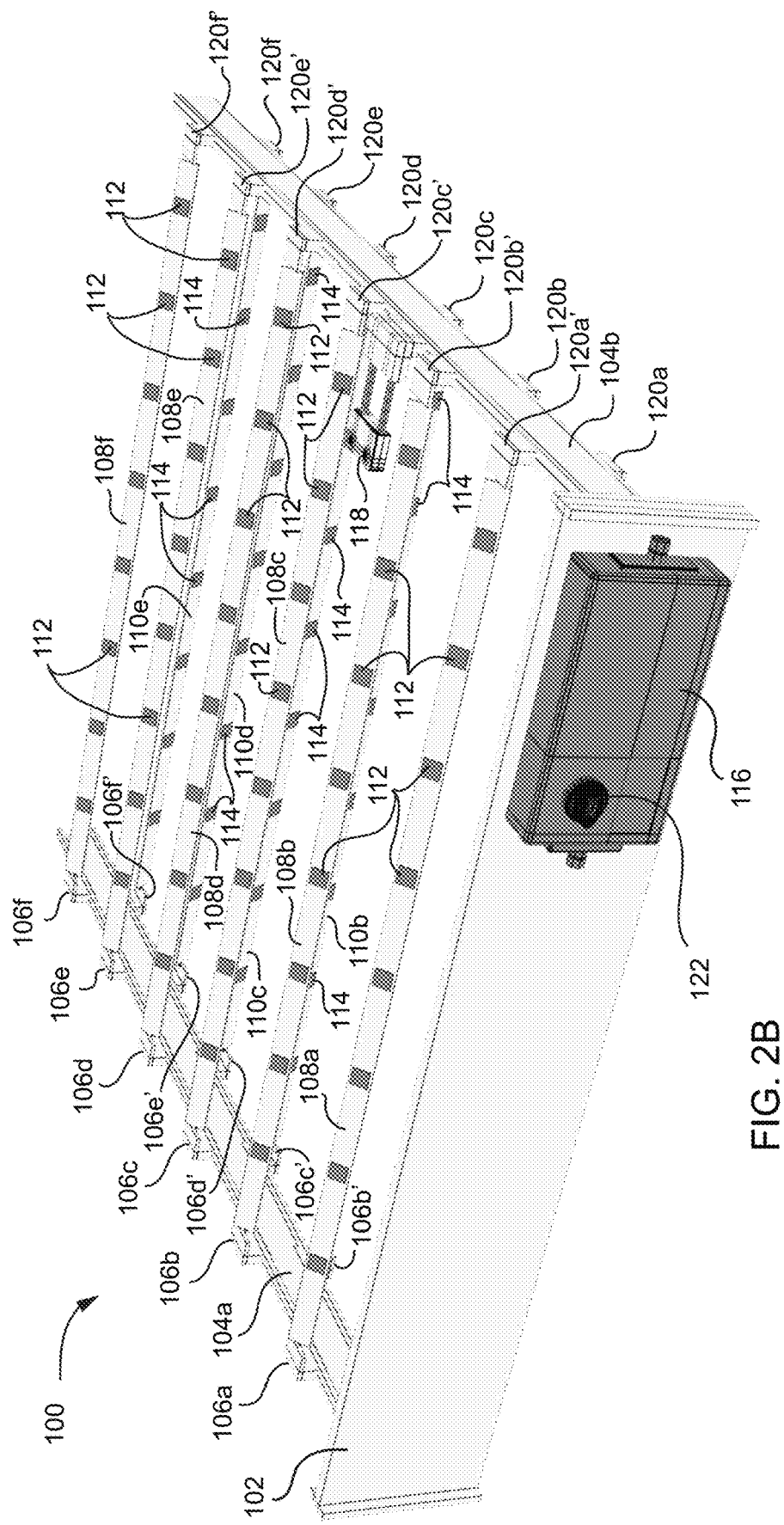
FIG. 2B is a front elevated perspective view of the example non-limiting air filter frame structure.
Figure 2C:
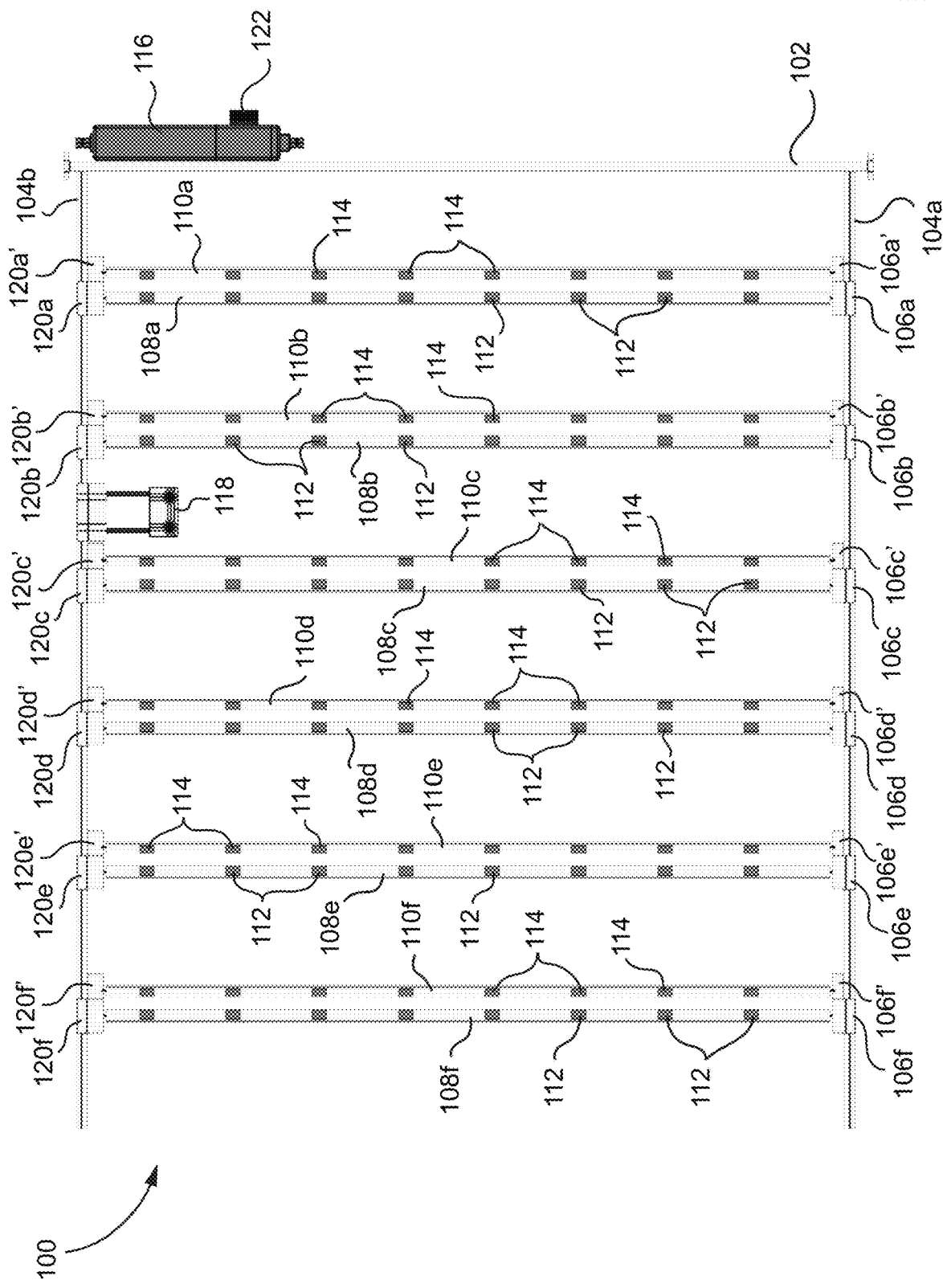
FIG. 2C is a top view of the example non-limiting air filter frame structure.
Figure 2D:
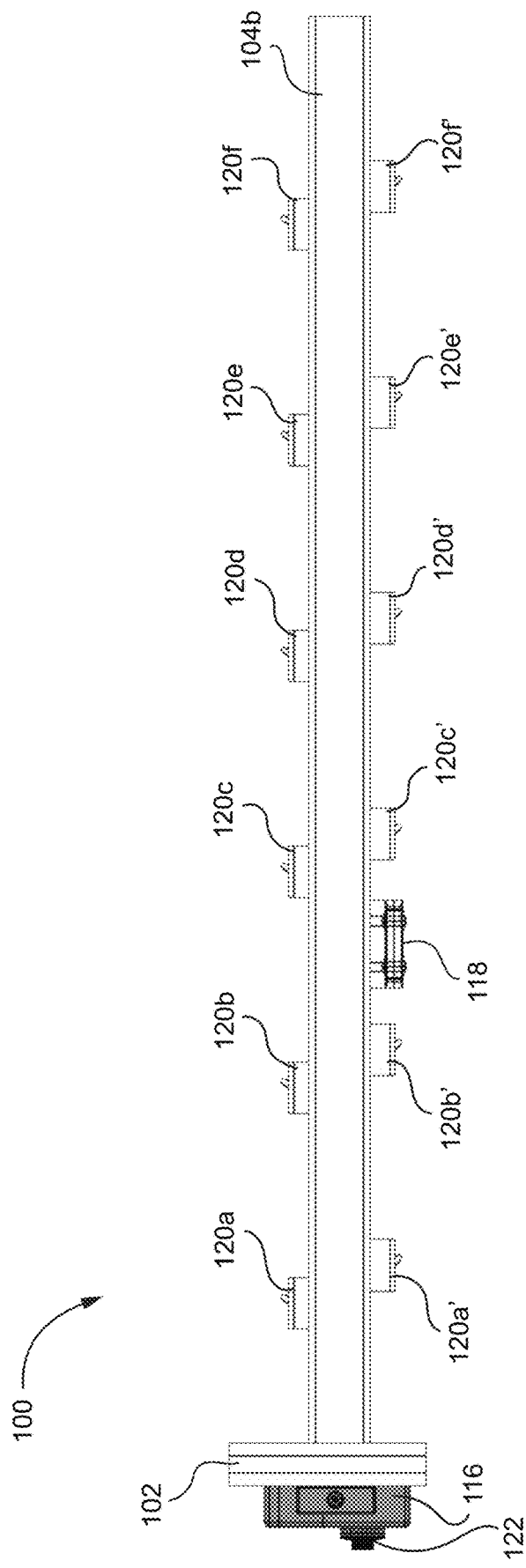
FIG. 2D is a side view of the example non-limiting air filter frame structure.

FIG. 1 shows an example air handling/recirculation system including a modular air filter encapsulation system 100. The FIG. 1 system can comprise a conventional HVAC system including an inlet air vent (bottom), a blower (to pull air in through the inlet air vent and propel it through the HVAC system), a heat exchanger (which may add heat to and/or remove heat from the propelled air flow), and an outlet air vent (top) that delivers air to one or more outlet vents. The FIG. 1 system further includes a modular air filter encapsulation system 100 placed in the path of the air flow such that all air that recirculates through the air handling/recirculating system must pass through the encapsulation system. The module air filter encapsulation system 100 in this embodiment includes a conventional air filter element that entraps small airborne particles (dust, droplets, aerosols, etc.) to prevent them from recirculating through the system.

In the example embodiment, a UV-C germicidal LED illumination system is provided on a frame or housing that holds, surrounds and/or encapsulates the conventional air filter element. The illumination system is configured to irradiate one or both sides of the undulating surfaces of the conventional air filter element and/or inflow air into the filter element and/or outflow air out of the filter element. The illumination system provides sufficient intensity of germicidal ultraviolet light to kill pathogens such as bacteria and viruses.

FIG. 1 shows the frame or housing and associated filter element in a horizontal orientation within the air handler. However, the frame or housing and associated filter element could be oriented vertically, or in any other orientation. Similarly, the FIG. 1 example shows a planar rectangular frame or housing or associated filter element but other embodiments can have any desired shape such as non-planar, three-dimensional, circular, ellipsoid, pentagonal, octagonal, or shaped in any multi-sided shape. The particular shape, structure and size of the filter or housing and associated filter element will in general depend on the particular application.

FIGS. 2A-2D show different views of a modular air filter encapsulation system 100 that supports air filters of various designs each using different embodiments, each comprised of arrays of UVC LEDs, rotating fins supporting each array in optimal orientation for maximum illumination and angles. The system further comprises a power control module designed to regulate power to sensors and each LED element on each UVC array.

In more detail, FIGS. 2A-2D show a frame comprising a planar faceplate 102 and first and second perpendicularly-extending parallel grooved frame side projections 104a, 104b spaced and dimensioned to define an active filtering space that can accommodate and accept a conventional air filter element. Example spacing/dimensions may be to accommodate conventional disposable or non-disposable/reusable or non-reusable residential, commercial, industrial or other air filter elements such as 10"×10"×1", 12"×12"×1, 12"×12"×2," 14"×20"×1", 14"×20"×2", 15"×20"×1, 15"×20"×2", 15"×20"×3", or any other standard or non-standard filter element in any shape, size, dimensions and materials. Some example frames may accommodate filter elements that are non-planar and/or non-rectangular such as cabin air filters of various different configurations, filter sheets or rolls, or other filter arrangements or configurations. Example frames may accommodate filter elements with any maximum efficiency reporting value (MERV) ratings such as MERV 8 to 13.

Figure 3A:
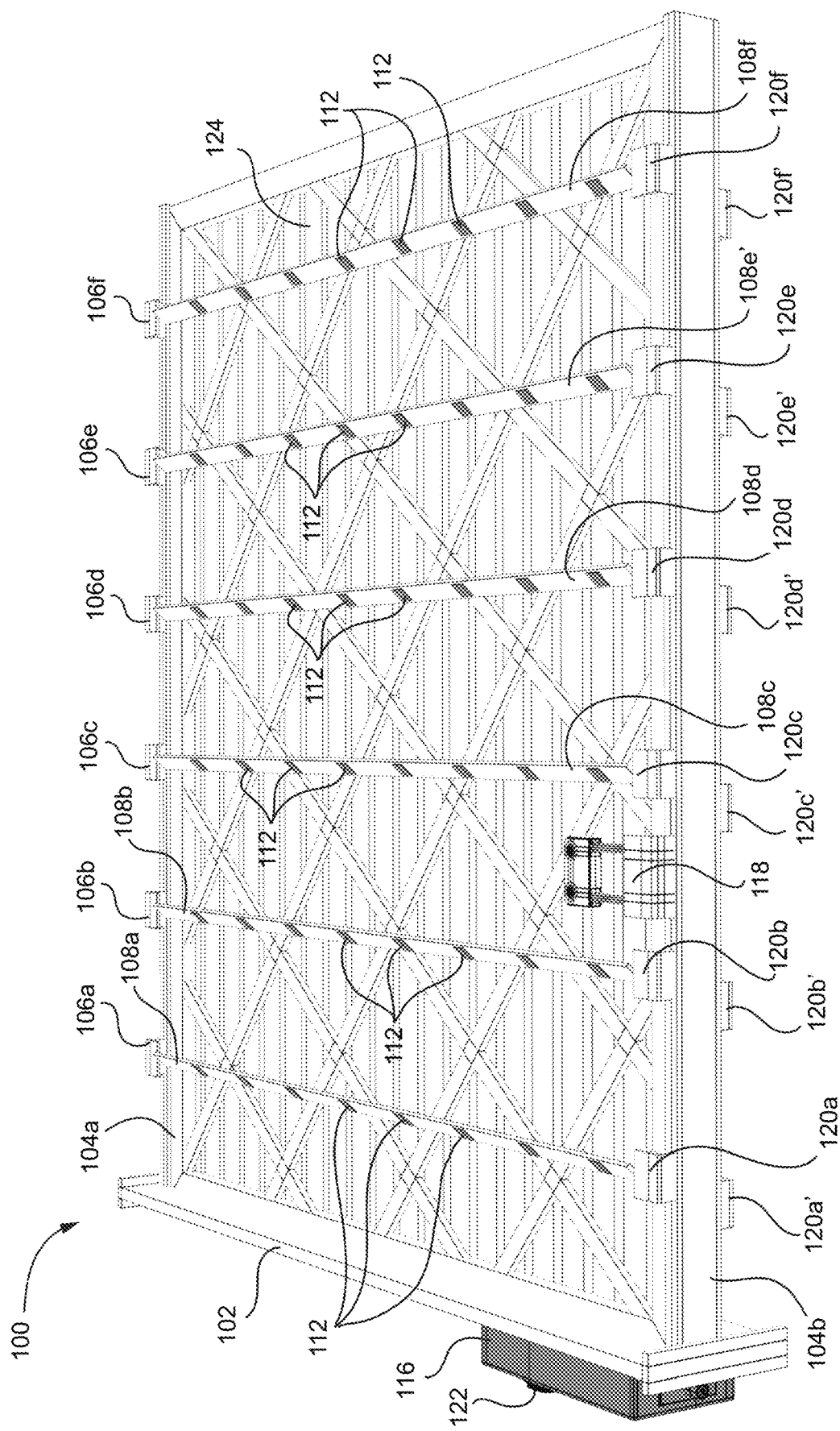
FIGS. 3A, 3B, 3C show the FIG. 2A, 2B, 2C views respectively of the air filter frame structure with a conventional air filter element inserted therein.
Figure 3B:
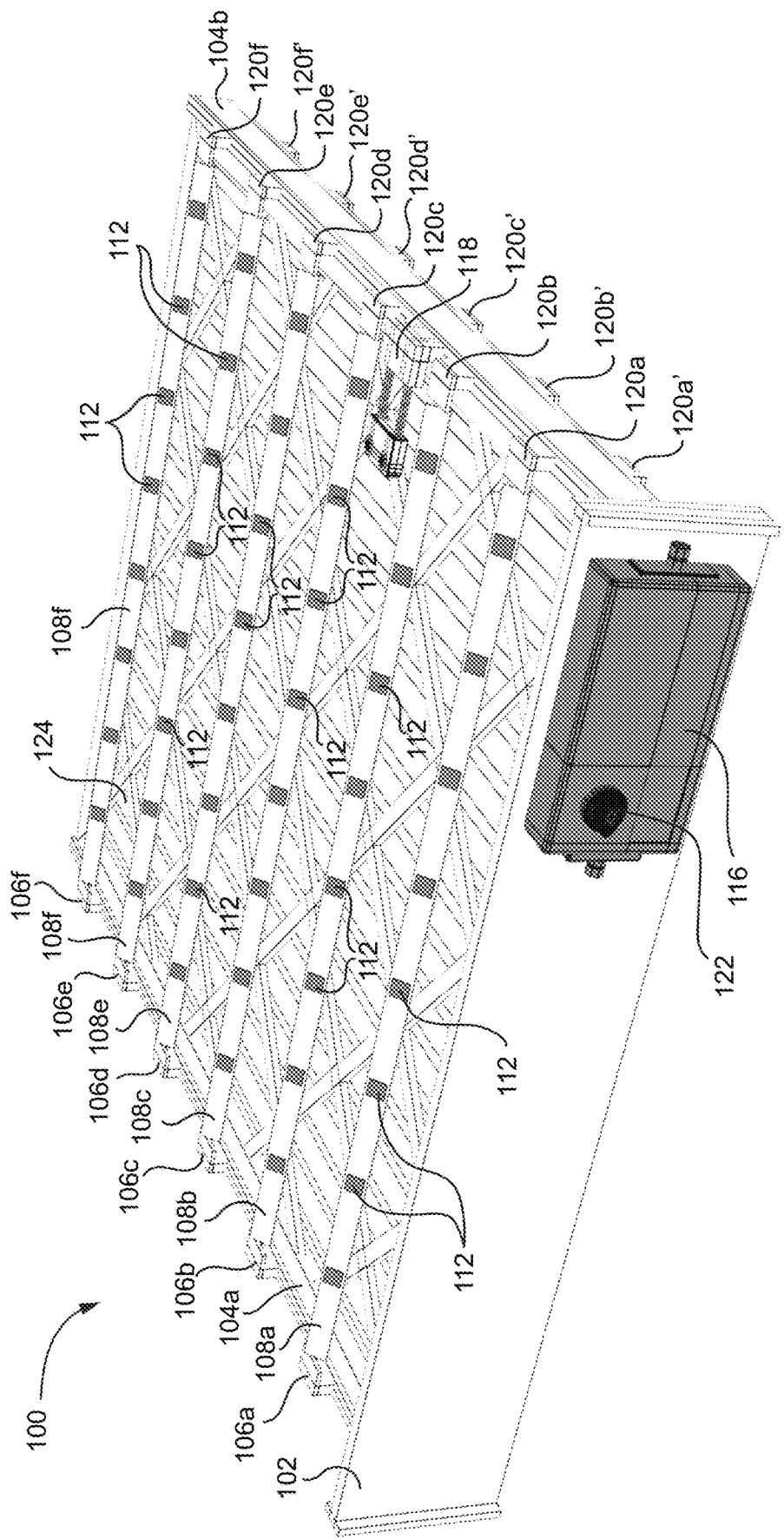
Figure 3C:
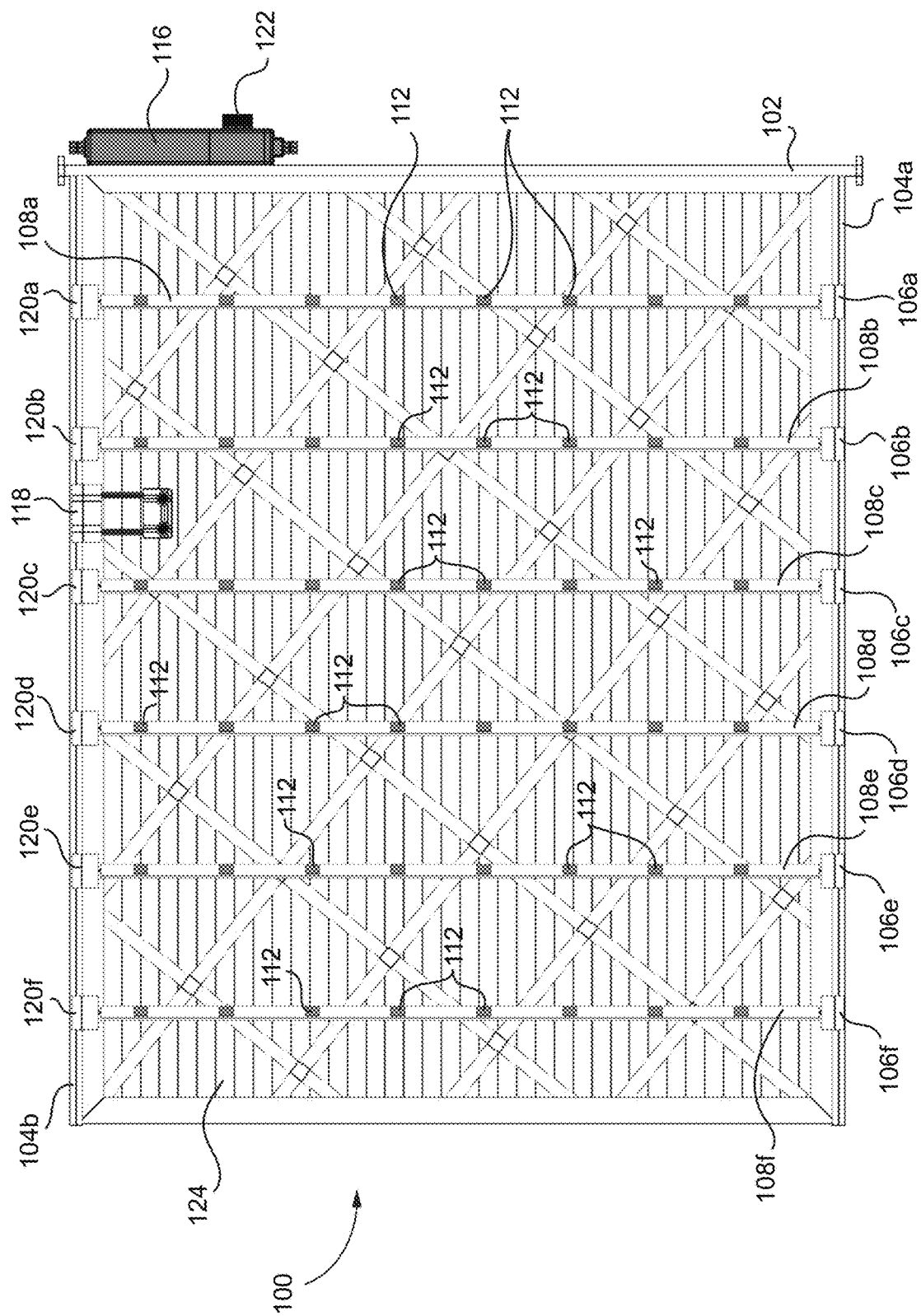

FIGS. 3A, 3B and 3C show the FIG. 2A-2D encapsulation arrangement with a filter element 124 in place. The filter element seals tightly to and is held and surrounded by the frame elements 102, 104 to ensure that all air flow must pass through the filter element. UV arrays 108, 110 are arranged and spaced so that all filter element 124 surfaces are illuminated and ingress and egress air flow is also illuminated for sufficient time with sufficient intensity to destroy pathogens.

As air moves through an HVAC system, air filters trap and collect large and small particles such as dust, allergens and microorganisms. According to the American Society of Heating, Refrigerating and Air-Conditioning Engineers (ASHRAE), this filtration helps provide healthier indoor air quality. A MERV rating of ≥13 (or ISO equivalent) is efficient at capturing airborne viruses, and MERV 14 (or ISO equivalent) filters are preferred. High efficiency particulate air (HEPA) filters are more efficient than MERV 16 filters. Generally, particles with an aerodynamic diameter around 0.3 μm are most penetrating; and efficiency increases above and below this particle size. Overall effectiveness of reducing particle concentrations depends on several factors such as:

Filter efficiency
Airflow rate through the filter
Size of the particles
Location of the filter in the HVAC system or room air cleaner.

In example embodiments herein, the frame 102, 104a, 104b supports one or more ultraviolet (UV) light emitting arrays 108, 110. In one embodiment, such UV light emitting arrays 108, 110 are evenly or unevenly distributed across the surface of the filter element to provide sufficient UV illumination on the surface(s) of the filter and in ingress and egress air flows. In many embodiments, the filter element is corrugated or undulating to increase filter surface area, creating a meandering or undulating filter surface topography. The UV illumination arrays 108, 110 are in one embodiment disposed and spaced above and across the filter element in such a way as to illuminate every part of such meandering/undulating filter surfaces as well as air flowing toward, away and/or through the filter element.

In some embodiments, UV arrays 108, 110 are respectively disposed on each side (both ingress and egress) of the filter element. In some embodiments, UV arrays 110 may be disposed only on the ingress side of the filter element or UV arrays 108 may be disposed only on an egress side of the filter element. In some embodiments, the UV arrays 108, 110 are structured to illuminate the filter surface(s) as well as ingress or egress air flow. In other embodiments, the UV arrays 108 on one side of the filter element may be used to illuminate the filter surfaces and/or the ingress/egress air flow in a first manner and the UV arrays 110 on other side of the filter element may be used to illuminate the filter surfaces and/or the ingress/egress air flow in a second manner different from the first manner. For example, the UV illumination on one side of the filter element may illuminate the filter surfaces but not the air flow, and the UV illumination on the other side of the filter element may illuminate the air flow but not the filter surfaces. In some embodiments, the UV arrays 108, 110 may contact or be integrated directly into the filter element instead of being spaced apart and above the filter element.

In the example shown, each UV array 108, 110 may comprise a longitudinal strip of plastic or other material that bears a plurality of light emitting diode illuminators 114 and associated electrical and/or data conductors. The number of UV illuminators 114 and their arrangements and spacings may depend on a number of factors including the filter element size, the type of filter element, the air flow rate, the degree of germicidal protection needed, the power and field of view of illuminators 114, and other factors. Similarly, the number of arrays 108, 110 on the respective sides of the filter element may depend on various factors including the size and shape of the filter element, the air flow rate, the degree of germicidal protection, the power and field of view of illuminators 114, and other factors. Ingress and egress sides of the structure can have different numbers of arrays 108, 110, or there may be an array 108 on one side of the filter element for each array 110 on the other side of the filter element. The arrays 108, 110 may be in registry to one another, offset from one another, or have no positional correspondence with respect to one another. In the embodiment shown the arrays 108, 110 are parallel to one another, but in other embodiments the arrays 108 can be oriented at right angles to the arrays 110, or may be oriented at any desired orientation relative to the arrays 110. The arrays 108, 110 in the embodiment shown are at right angles to side arms 104 and parallel to front face 102, but in other embodiments the arrays may be oriented parallel to the side arms and at right angles to the front face, or the arrays may be oriented at any angle relative to the side arms and front face. In the embodiment shown all arrays 108 are parallel to one another and all arrays 110 are parallel to one another, but in some embodiments arrays 108 can have different orientations relative to one another and arrays 110 can have different orientations relative to one another. In the embodiment shown arrays 108 are coplanar and arrays 110 are coplanar so they are equidistant from the filter surface(s), but in other embodiments arrays 108 may lie in different planes and/or arrays 110 may lie in different planes to provide different distances between the filter element and the arrays and/or to accommodate non-planar filter elements.

As can be seen in FIGS. 2A-2D, the UV arrays 108, 110 in one embodiment each comprise a thin strip of flexible or rigid material. These UV array strips are shown as having different orientations relative to the frame or housing 102, 104. In particular, in this embodiment the strips comprising UV arrays 108 on one side of the filter element are oriented at about the same orientation of an analog clock hand pointing at 2 o'clock, and the strips comprising the UV arrays 108 on the other side of the filter element are oriented at about the same orientation of an analog clock hand pointing at 10 o'clock, such that there is a 60 degree or so angle orientation difference between a UV array 108 and a corresponding UV array 110. These orientations are adjustable in one embodiment, and fixed in other embodiments.

Figure 4:
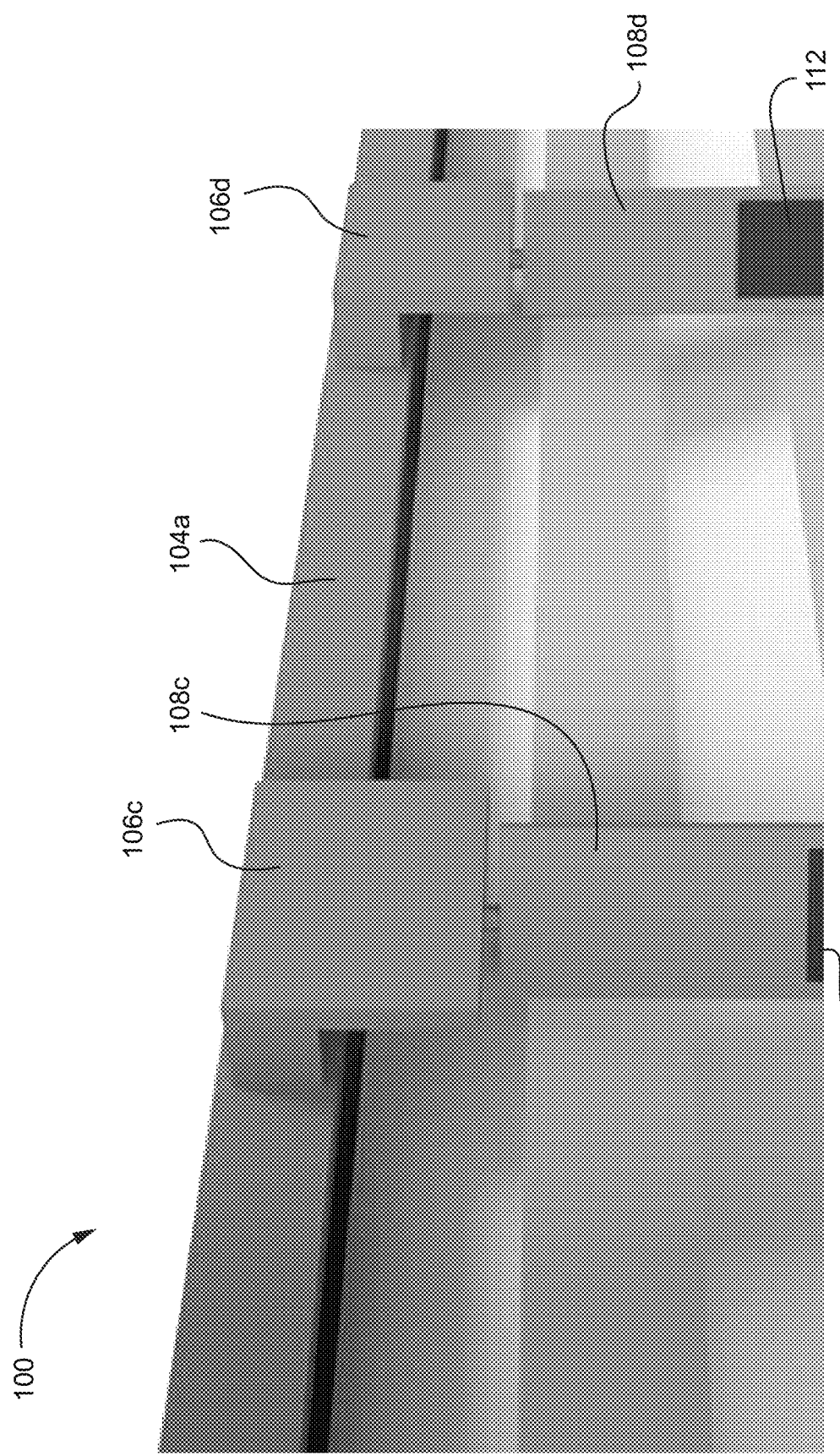
FIG. 4 is a magnified view of rotating fins that support UVC LED arrays. The direction of each fin is designed based on airflow and filter size. Each fin rotates at an appropriate angle, designed for maximum exposure/irradiance and preventing shadowing effects.

FIG. 4 is a magnified view of rotating/rotatable fin structures 106, 120 that support UVC LED arrays 108 (similar fins 106, 120 may support LED arrays 110) used to set the orientations of the arrays. The FIG. 4 fin clips support and rotate UVC arrays 106, 120 to proper or desired angles. The rotation of each fin 106, 120 is designed specifically for maximum irradiance and exposure of photons received by surface area as UVC LEDs are illuminated, and protection of eye or skin of human. The direction of each fin 106, 120 is designed based on airflow and filter size. Each fin 106, 120 rotates at an appropriate angle, designed for maximum exposure/irradiance and preventing shadowing effects. UVC arrays are spaced and aligned relative to one another, using fins to orient them while ensuring they do not interfere with insertion and removal of replaceable disposable filter elements. In some embodiments the fins 106, 120 are user-adjustable and in other embodiments they are adjustable other than by a user or not adjustable.

Figure 5A:
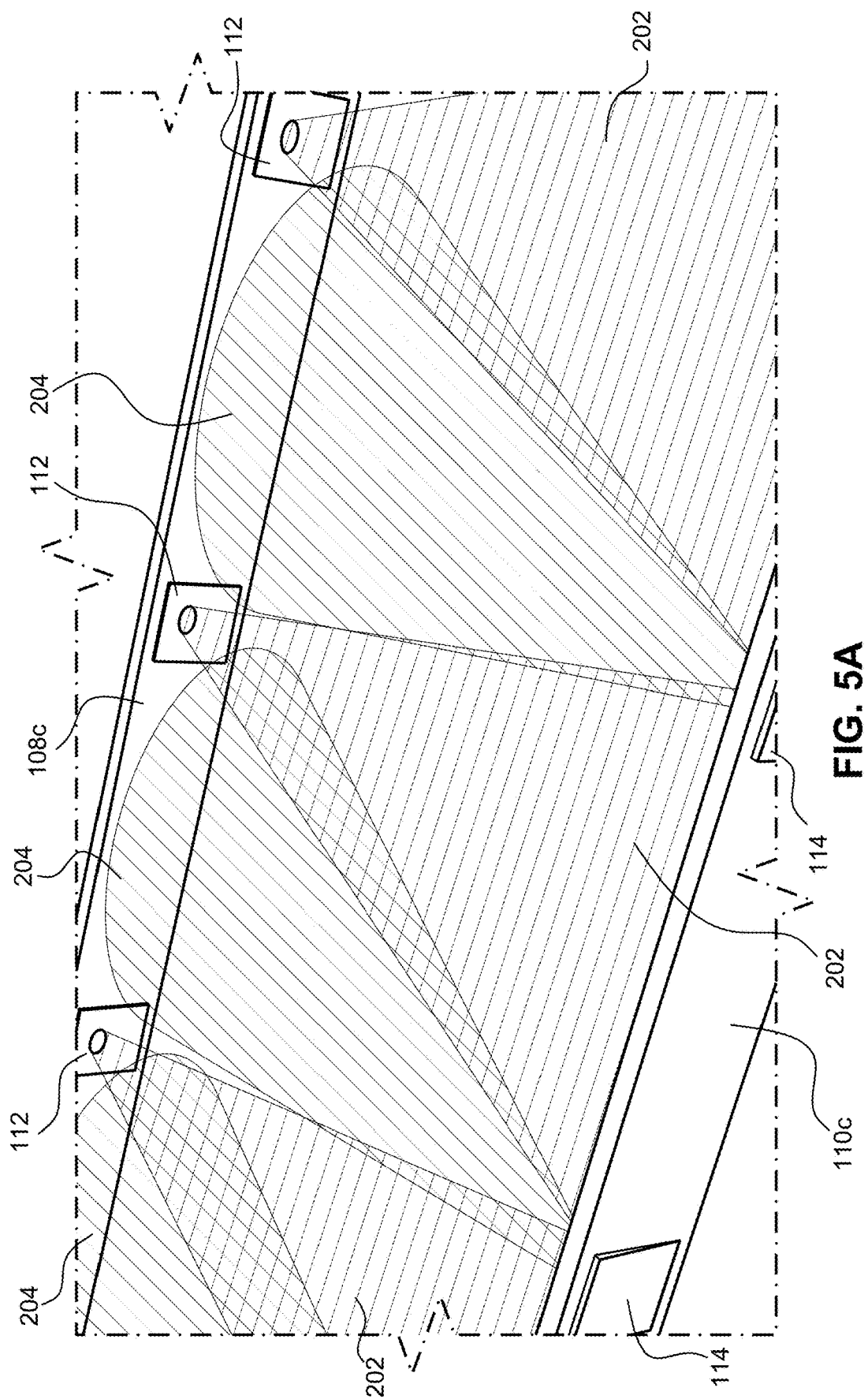
FIGS. 5A, 5B, 6A, 6B show example radiation coverage of UVC LED arrays.
Figure 5B:
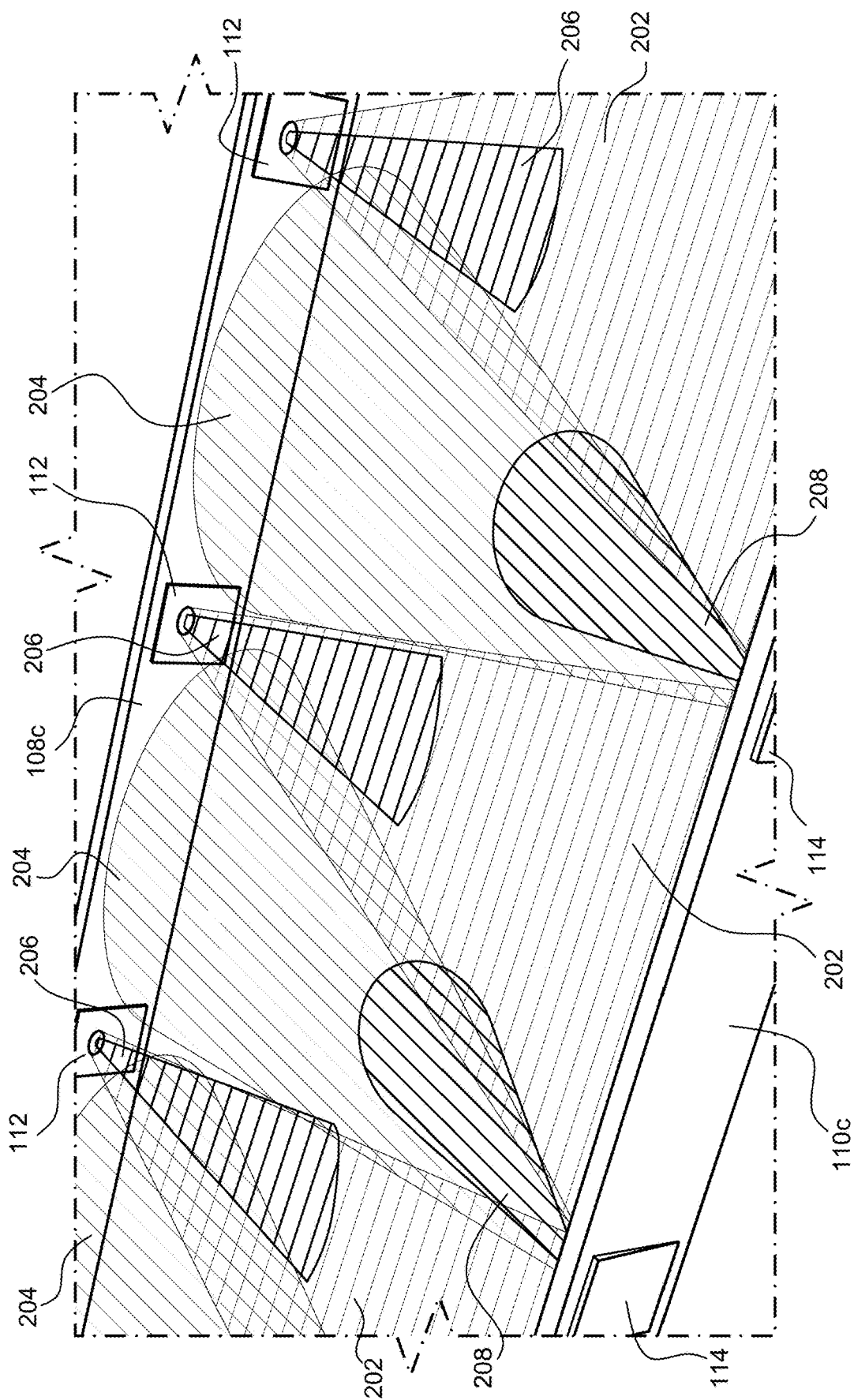

FIGS. 5A and 5B each show top views of LED irradiance on the filter. In more detail, FIGS. 5A, 5B show example interdigitated/overlapping illumination intensity patterns of respective opposing/facing light element elements 112 on adjacently positioned array strips 108c, 110c FIG. 5B shows show example interdigitated/interlocking illumination intensity patterns of adjacent strips 108c, 110c can lie in different planes to ensure adequate three-dimensional light penetration through an ingress or egress air flow.

Figure 6A:
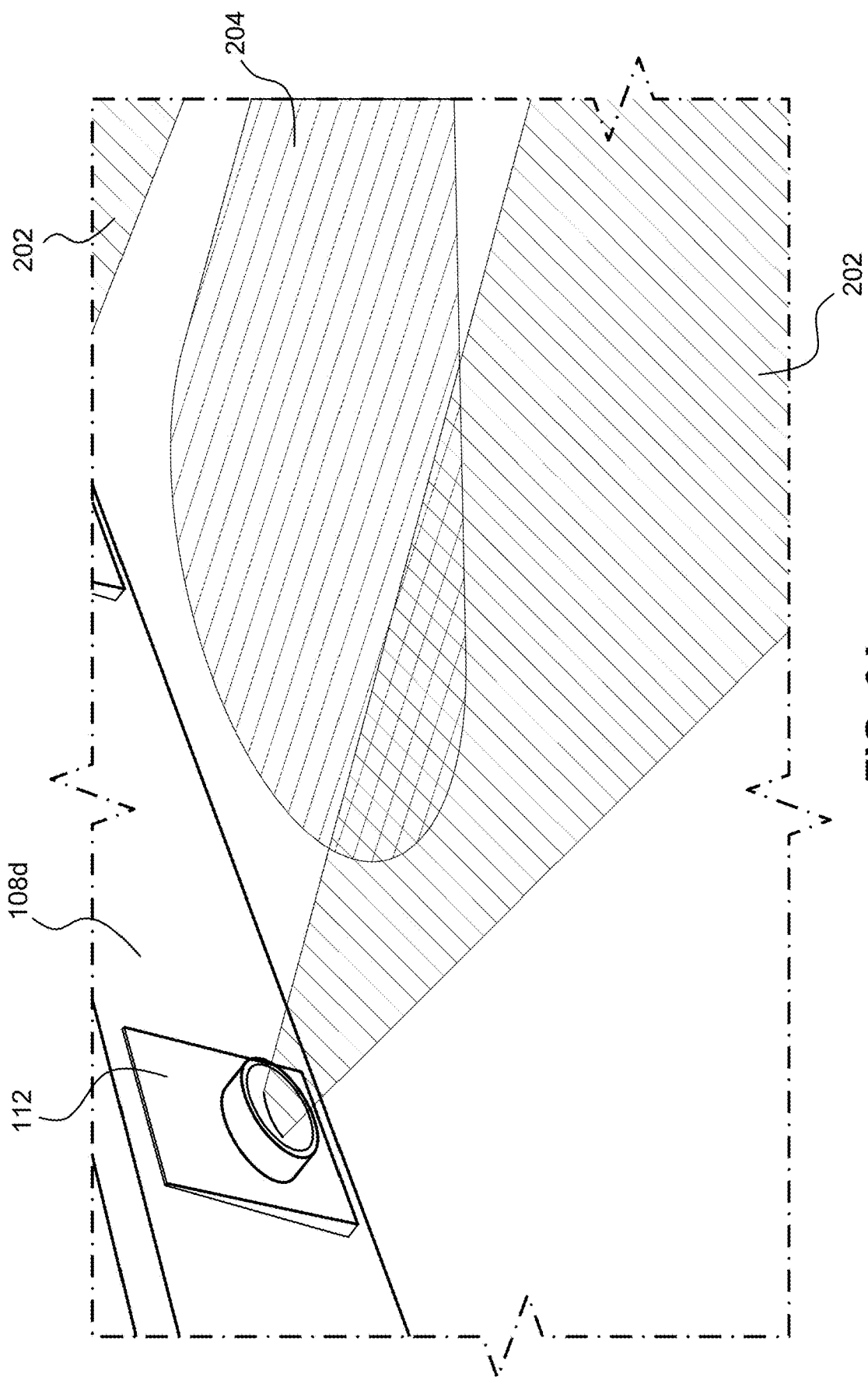
Figure 6B:
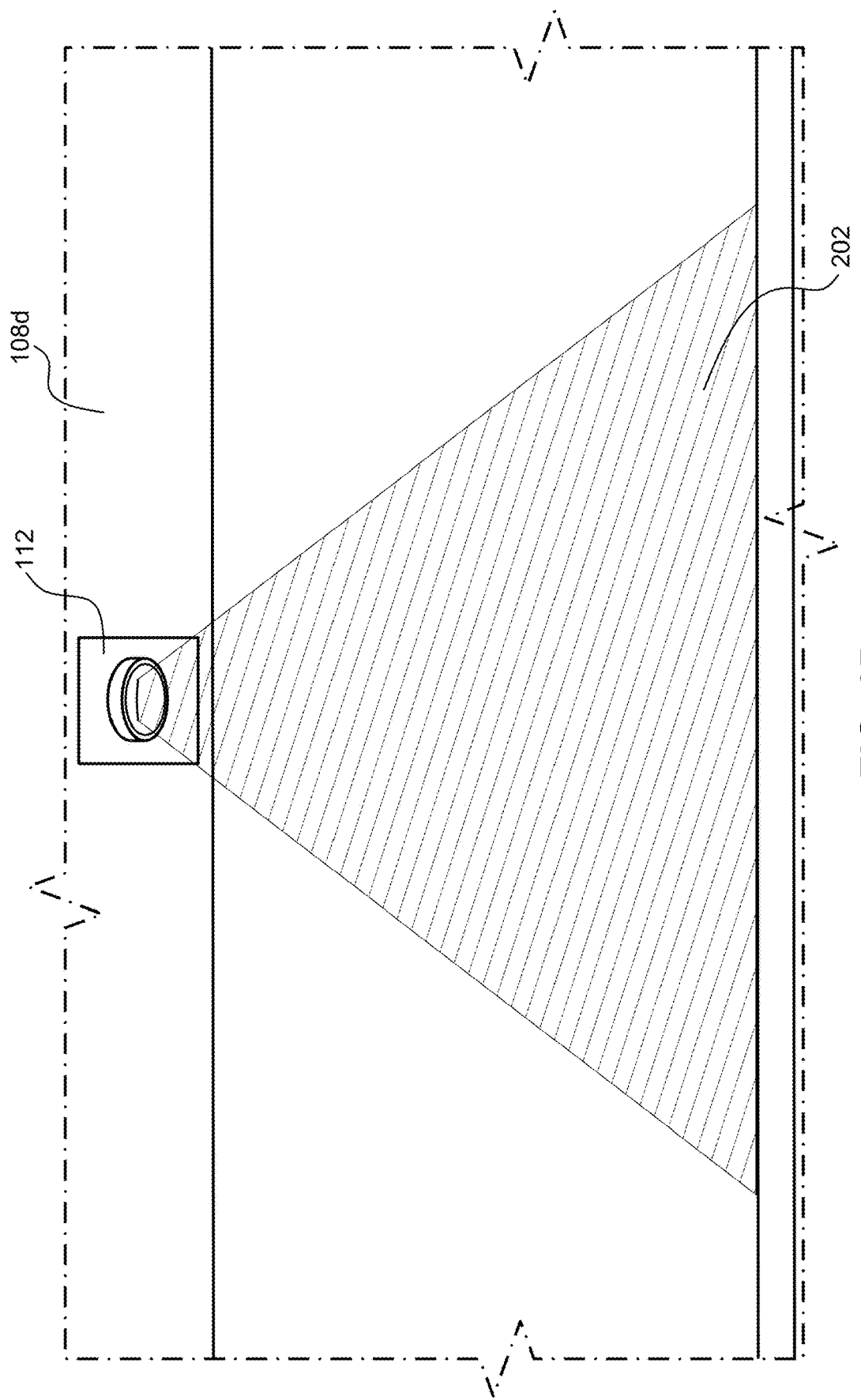
Figure 7A:
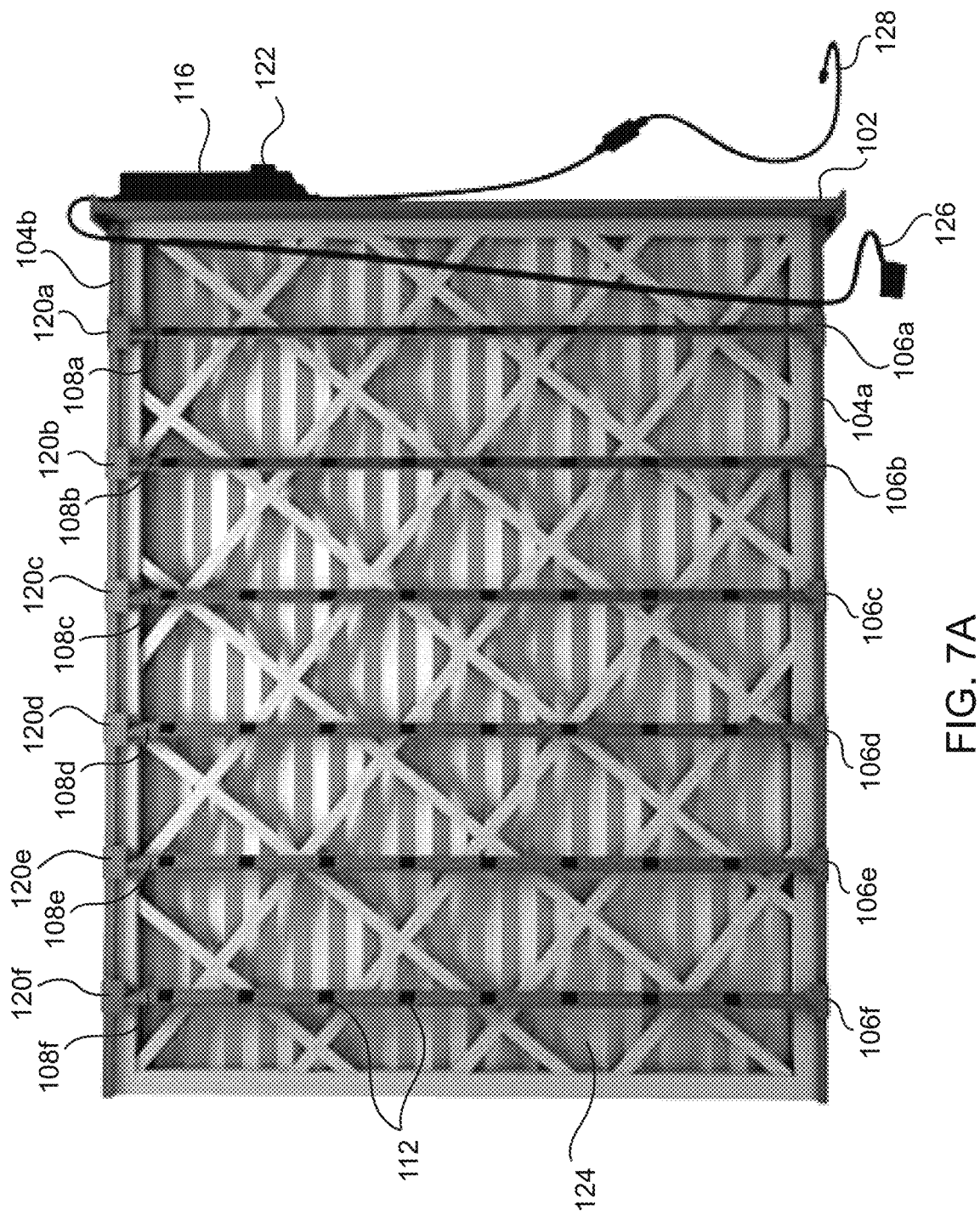
FIGS. 7A, 7B, 7C, 7D shows an example air filter encapsulation unit (side 2) with UVC arrayed LEDs and power control unit placed at different orientations.
Figure 7B:
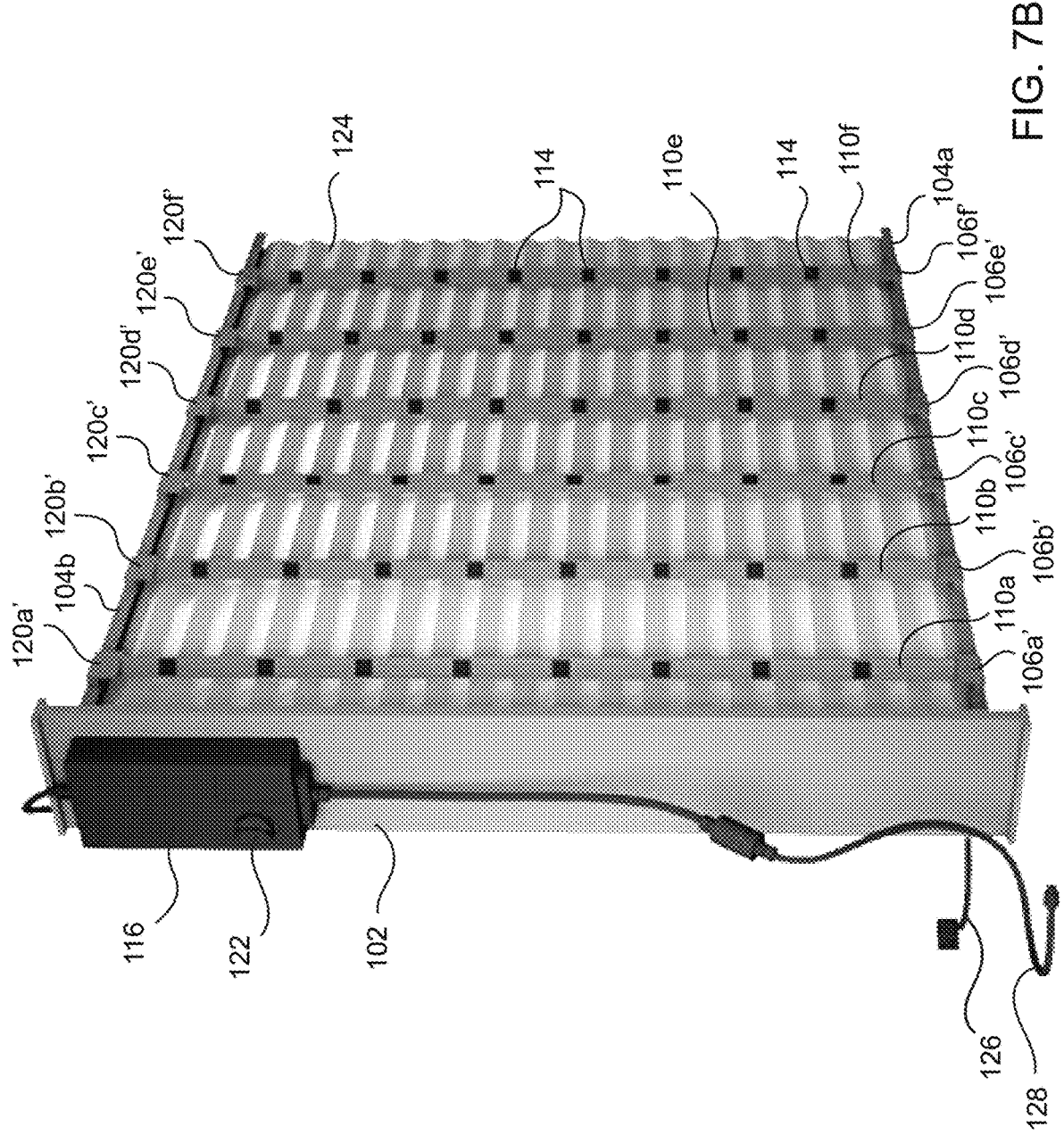
Figure 7C:
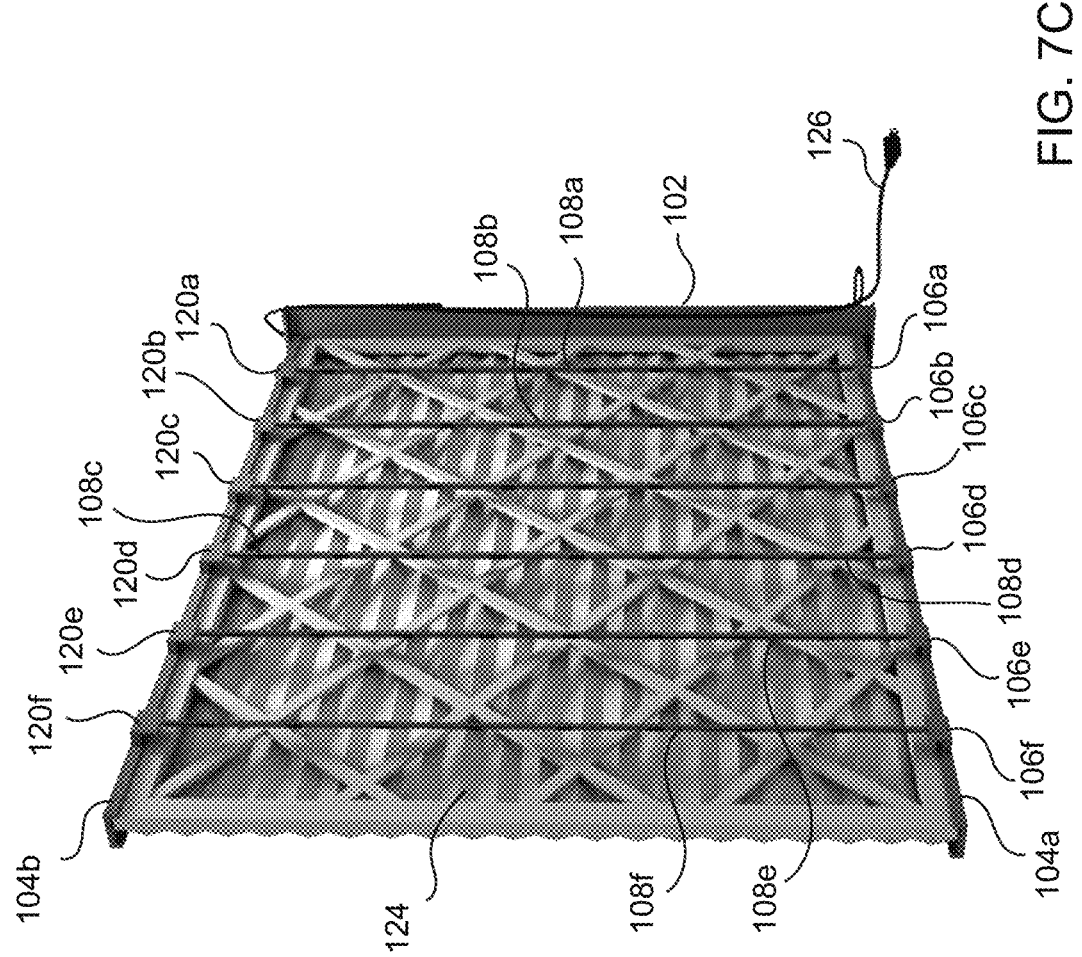
Figure 7D:
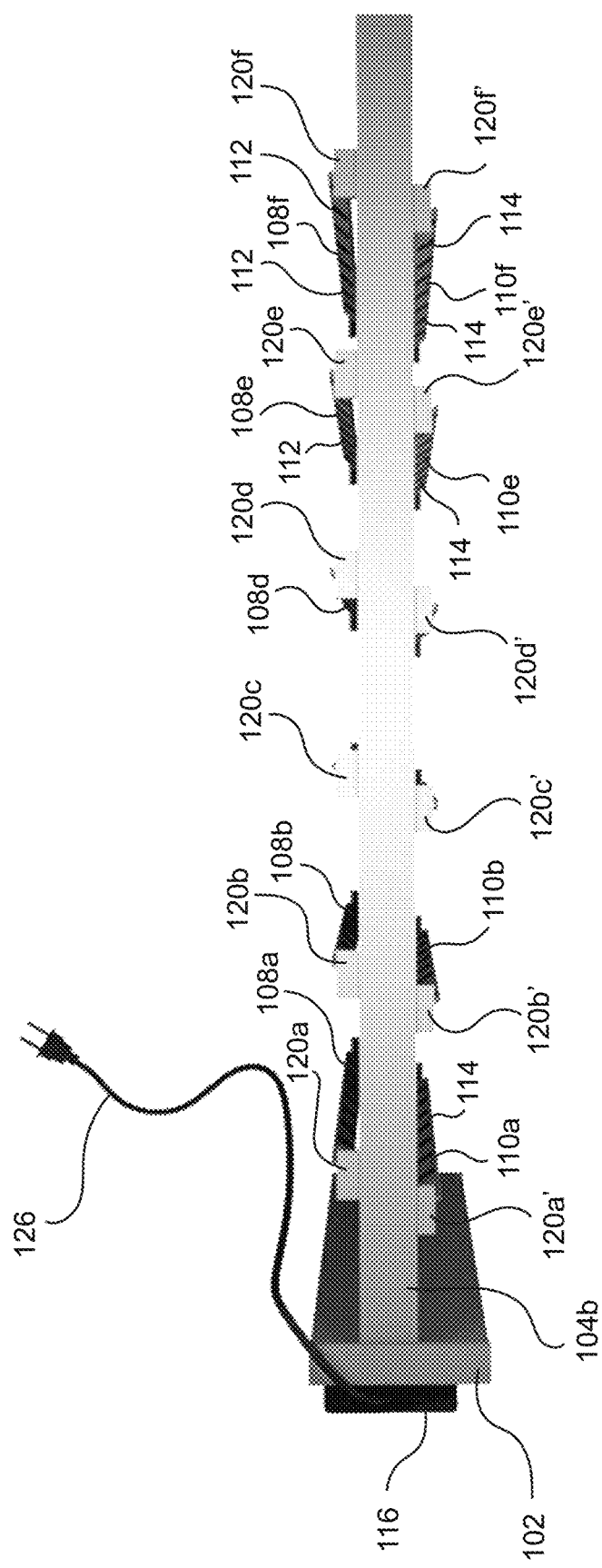

FIG. 6A shows an example side angled fin view of LED irradiance on the filter and FIG. 6B shows an example front angled fin view of LED irradiance on the filter.

Our system allows exposure of 6000 Joules/m2 for eliminating colonies of 6000-10,000 RNA viruses. As such, UVC LEDs are exposed at range of a few seconds to 60 an hour with closely spaced UVC LED arrays in vertical and horizontal direction. Our system allows logarithmic reduction of 1,000-10,000 colony forming units (CFUs).

FIGS. 7A-7D show additional views of an encapsulation system including UVC LED arrays 108, 110, controlled by a power module or circuit 116 and a housing that is adjustable in size and/or shape, such that each embodiment accepts and encapsulates an air filter 124. Each embodiment integrates UVC LEDs and air filter in the most efficient angle. Illumination angle of UVC LED strip is varied for maximum exposure. This allows positioning each LED at closest distance and helps avoid shadowing effects on air filter surface area with distinct geometric shape. The embodiments shown provide configurable arrays with placement and orientation altered manually or automatically to the shape of the air filter. Each array in vertical and horizontal directions may face towards side-1 of primary filter (inward or ingress air flow).

Further shown in a power and safety module 116 comprising an automatic shutoff mechanism, a detector to monitor airflow/rate and turn control system ON/OFF, maximum exposure on air intake side and outlet of the air filter. The safety module 116 uses sensors 118 in order to prevent exposure of UV rays to eyes or skin; and to avoid risk of skin burn. An electro-mechanical sensor automatically shuts off power to the UVC LED arrays when cover is opened. Sensors detects ambient temperature, smoke air flow, and carbon monoxide.

Figure 8:
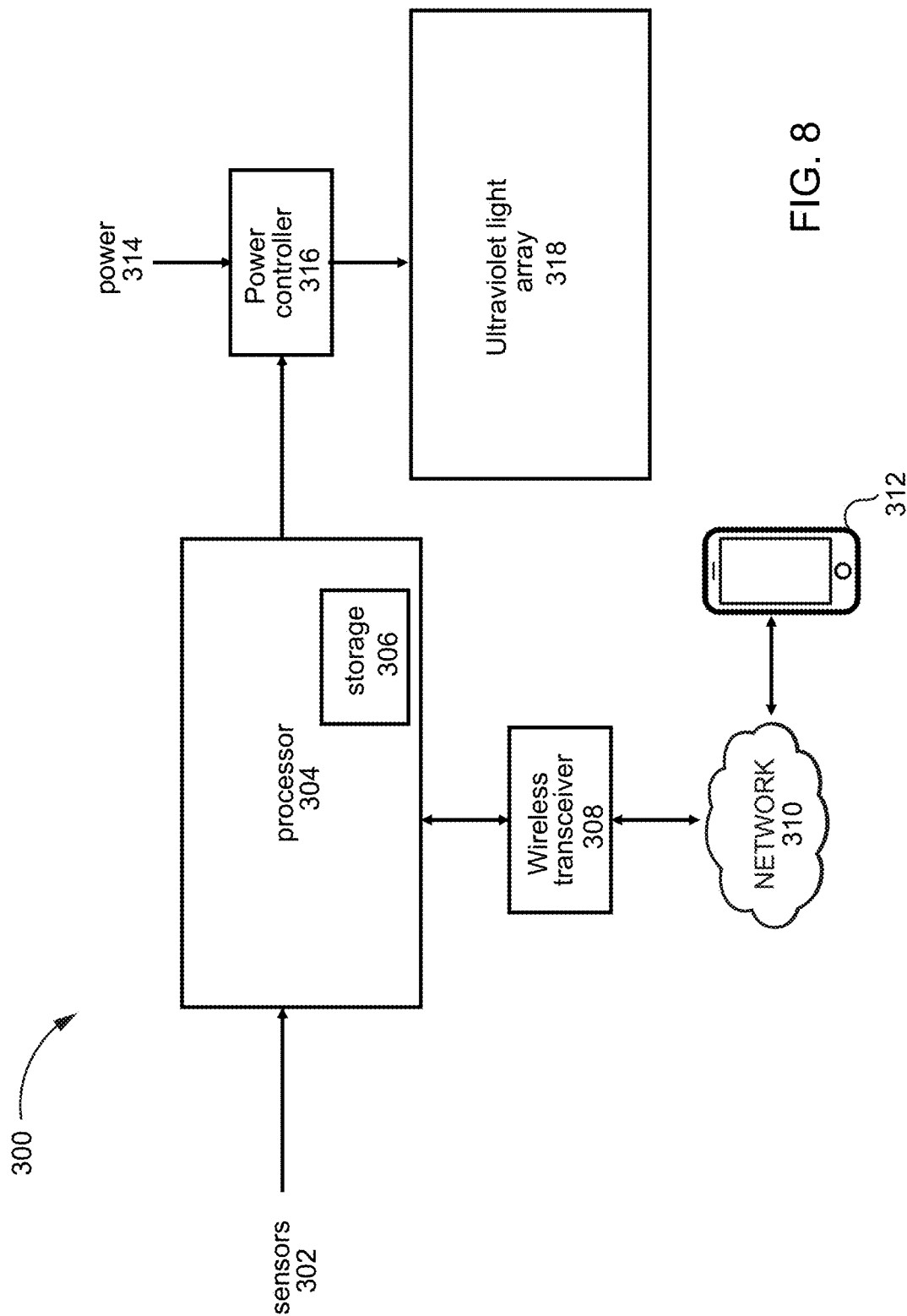
FIG. 8 is an example non-limiting block schematic circuit diagram.
Figure 9:
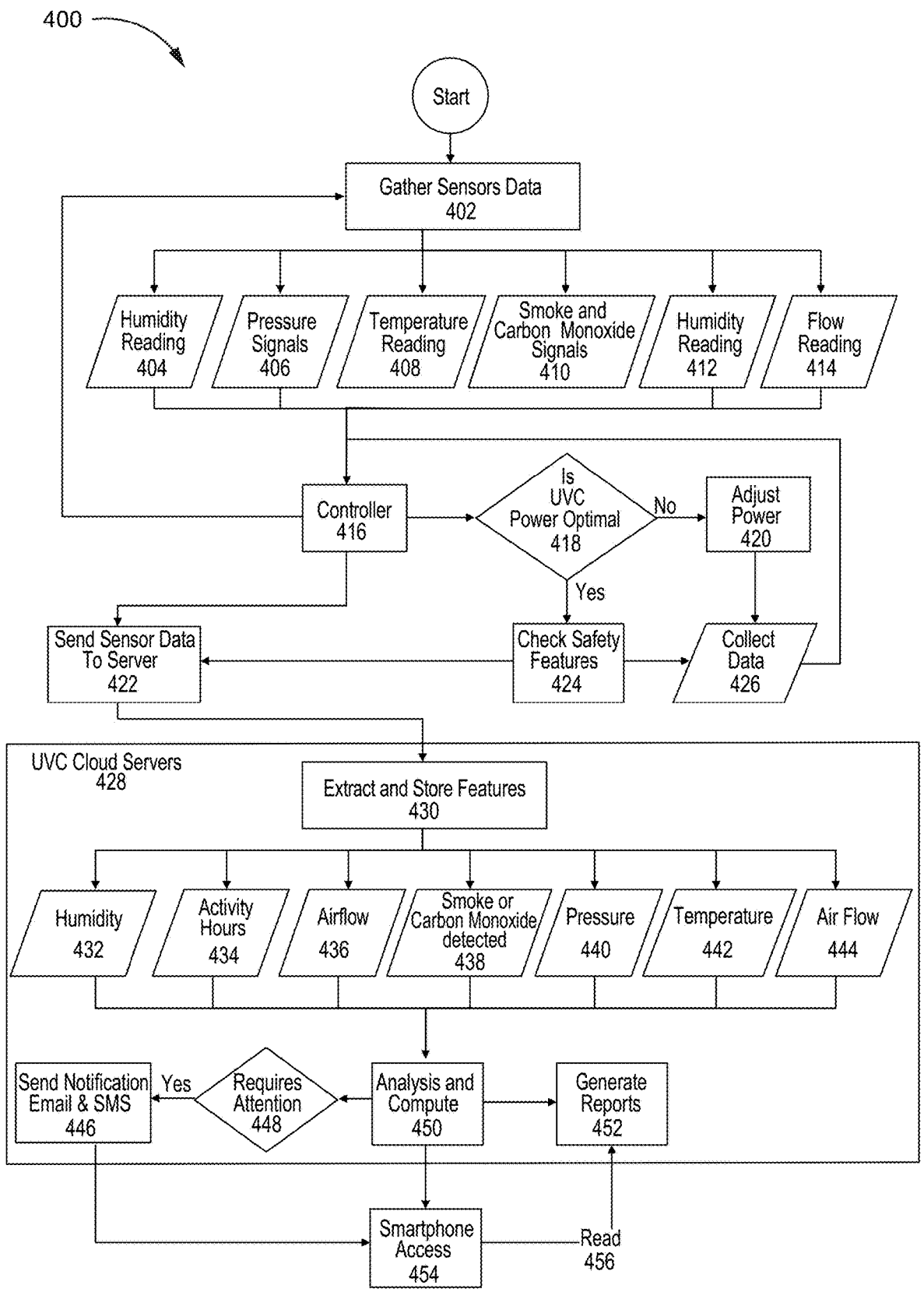
FIG. 9 is an example Block Diagram of an Air filter system and smart device app user-interface to sensor and control system of same.

FIGS. 8 and 9 show block diagrams of Air filter system and smart device app user-interface to sensor and control system. The FIG. 8 diagram shows a processor 304 that is connected to receive sensor signals from sensors 302 and generates a power control output for controlling a power controller circuit 316 supplying power to UV arrays 318 (108, 110). The processor 304 executes instructions stored in non-transitory storage 306 to perform the example operations shown in FIG. 9, which Figure also shows operations performed by a server/cloud device 310 and a smartphone or other smart user device 312. The processor can communicate via a wireless transceiver 308 with (an)other device(s) such as smart phone 312 via wireless protocols such as Bluetooth, WiFi, WiMAX, 5G or any other desired wireless protocol(s), either directly or via a server or other cloud device.

A WiFi enabled system is controlled with a smart device 312 and an app running on that same device to control settings and receive output signals. The WiFi-enabled control allows users to control the system remotely and notifies users of any functionality issues associated with the unit (FIG. 9, e.g., blocks 446-456). The app uses sensor outputs that monitor temperature, humidity, quality of air including smoke, carbon monoxide, airflow rate, condition of air filter (FIG. 9, blocks 404-414) and may include a power control feature to increase/decrease power to the UV arrays (FIG. 9, blocks 418, 420). Further, this app notifies users of any current and past usage, UVC system running condition, system usage in hours, and LED lifetime enabled by a timer (FIG. 9, blocks 432-444).

In one embodiment, the processor 304 varies the illumination the UV arrays 108, 110 produce (FIG. 9, block 420). For example, the processor 304 may vary the UV intensity depending on air flow rate, with higher intensities being commanded for higher rates. When the air handling system turns off or an access door is opened, the system can detect this and turn off (or down) the UV intensity to conserve power and UV light emitting diode life and reduce risks to humans. In one embodiment, the processor 304 can individually address and independently control the intensity and wavelength of light emitter 112 by using digital bus signals to address any particular light emitter and write digital intensity and/or wavelength parameters to control the intensity and/or wavelength of that particular light emitter. In another embodiment, the processor 304 addresses and controls the intensity and/or wavelength of each of LED strips 108, 110. In another embodiment, the processor 304 exercises on/off control over all of LED strips 108, 110 in common, which strips have predetermined fixed intensity and/or wavelength of have intensities that can varied depending on characteristics (e.g., voltage, duty cycle, etc.) of a power/driving signal.

Further Use Case

Figure 10:
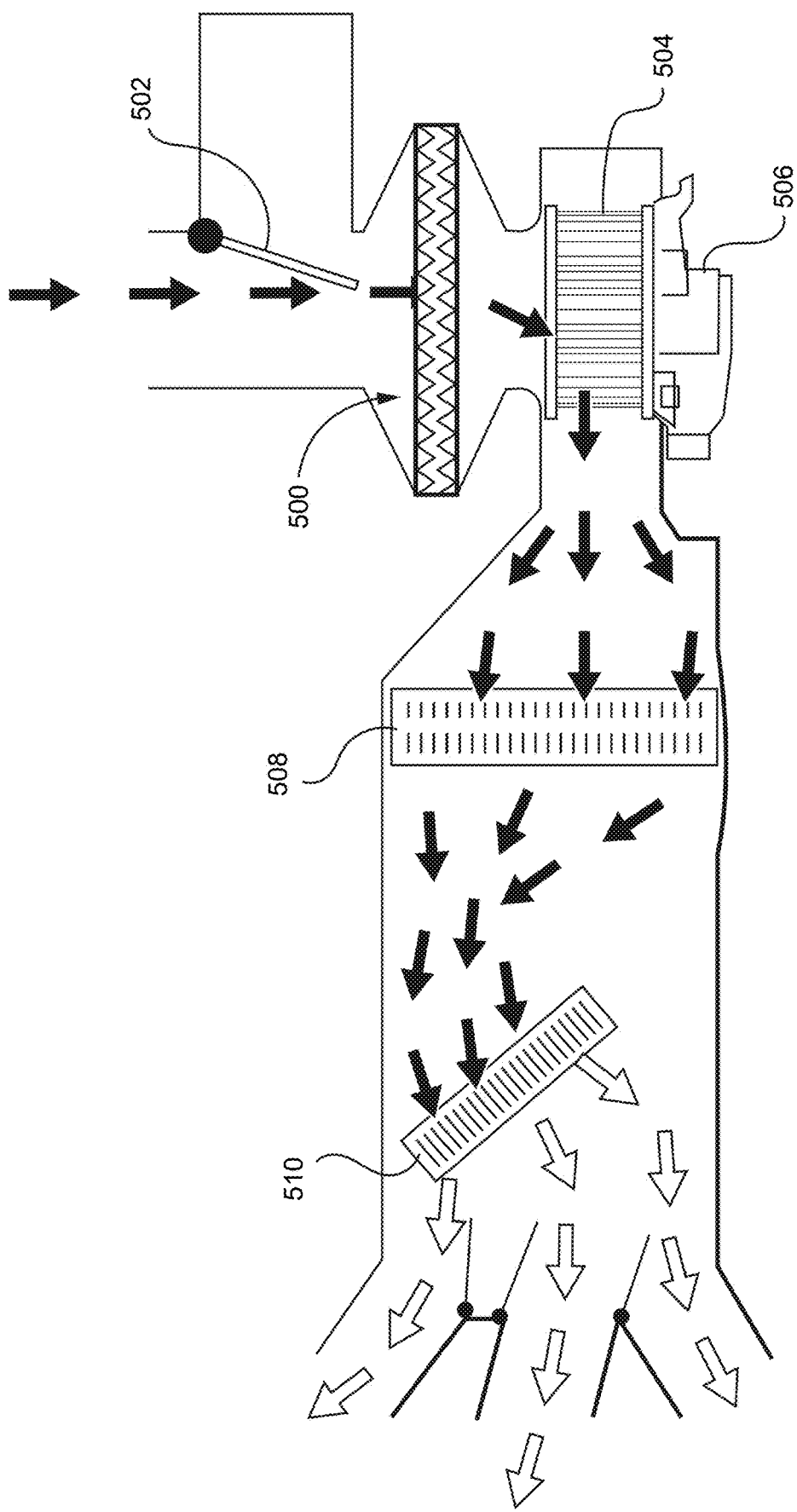
FIG. 10 shows an example automotive use cases for the air filter encapsulation system.

FIG. 10 shows an additional example use case for the disclosed encapsulated filter. FIG. 10 shows use, installation and placement of the encapsulated filter as a cabin air filter in a vehicle air recirculation system. In this example, recirculating air through a shutter or vent 502 flows through the UV encapsulated filter 500 under force of blower 504, which pushes the air through a heat exchanger 508 and a diverter 510 to output vents on a dashboard, cockpit or other parts of the vehicle. Other use cases such as mask filter elements, ventilator filter elements, vacuum cleaner filter elements, household fans or blowers, humidifiers or dehumidifiers, or any other device that moves or flows air that may be breathed by humans or animals, may benefit from application of the technology described herein.

Example 1

One embodiment of air filter encapsulation system is comprised of uniquely designed:
Air filter slot encapsulation system
UVC LED arrays
UVC array angle adjusters
Senor Module
Power Module.
The air cleaning system that support air filters of various designs using various embodiments, may each be comprised of
WiFi-enabled: WiFi enabled system is controlled with a smart device and an app to control settings and receive output signals
Safety module: In order to prevent exposure of UV rays to eyes or skin; and avoid risk of skin burn, an electromechanical sensor automatically shuts off power to the UVC LED arrays when cover is opened.
UVC LED Lifetime: In order to prevent overheating of power supply caused by over-aging UVC LEDs, two sensors provide user with approximated large signal resistance and small signal impedance, as indication of excess power dissipation due to degraded LEDs in each array.
Maintenance: A set of timers forewarn the user to change air filter at appropriated time.
The air filter encapsulation system may be comprised a Power control module designed to regulate power to sensors and each LED element on each UVC array comprising:
Safety shutoff feature
Detector to monitor airflow/rate and turn control system ON/OFF
Sensors monitor humidity
Regulate power level depending on airflow
Maximum exposure on air intake side and outlet of filter
Serial exposure synchronized on output side of filter
The air filter encapsulation system may be comprised a safety module, comprising output of:
Sensor that detects ambient temperature
Sensor that detects smoke in the air.
Sensor that detects carbon monoxide in the air.
Sensor that detects smoke
Sensor that detects Carbon monoxide
The air cleaner unit may comprise a housing that is adjustable, such that:
Adjustable to fit multiple standard sizes for residential air filters.
Adjustable to fit multiple standard sizes for commercial air filters.
Each embodiment encapsulates an air filter.
The embodiment integrates UVC LEDs and uses directional positioning to maximum exposure to avoid shadowing effects and positioning at closest distance.
The array is configurable wherein the placement and orientation can be altered manually or automatically adjusted to the shape of the air filter. Array placement, orientation and power design of UVC array maximize air filter surface and intake and outlet with irradiance (radiant power received by surface) of 2000-8000 micro-watt/cm2 with fluence (UV exposure dose rate of 10-80 Joules/m2/Sec.
An array of UVC Germicidal Disinfection LED is used to eliminate pathogens such as bacteria, mold, mildew allergens, and deactivate viruses such as SARS CoV-2.
Fin clips support and rotates UVC arrays to proper angles.
Rotation of fins are designed specifically for maximum irradiance and exposure of photons received by surface area as UVC LEDs are illuminated.
Rotation of fins are designed specifically for protection of eye or skin of human. Protection control unit resets power to the UVC LED array.
Rotation of fins are designed specifically for protection of eye or skin of human. Protection control unit resets angle of illumination to 0°.
A UVC Germicidal embodiment is arrayed UVC in:
vertical and horizontal directions facing towards side-1 of primary filter (inward air flow) [#]
vertical and horizontal directions facing opposite of side-1 of primary filter (outward air flow) [#]
vertical and horizontal directions facing towards side-2 of primary filter (inward air flow) [#]
vertical and horizontal directions facing opposite of side-2 of primary filter (outward air flow)
The UVC Germicidal embodiment is arrayed UVC in:
vertical or horizontal directions facing towards side-1 of primary filter (inward air flow) [#]
vertical or horizontal directions facing opposite of side-1 of primary filter (outward air flow) [#]
vertical or horizontal directions facing towards side-2 of primary filter (inward air flow) [#]
vertical or horizontal directions facing opposite of side-2 of primary filter (outward air flow).
WiFi-enabled control allows users to control the system remotely:
Notifies users of any functionality issues associated with the unit.
Notifies users of outputs of:
Sensor that detect poor quality of air
Sensor that detects aged air filter
Sensor that detects humidity of air.
Sensor that detects temperature of air.
Sensor that detects smoke in the air.

Sensor that detects carbon monoxide in the air.
Sensor that detects rate of airflow/pressure.
Notifies users of any current and past activities
System notifies UVC system users running conditions. The system alerts the user of poor system performance, such as, detection of significant reduction in airflow and alarms a possible system maintenance or aged air filter.
Provides daily, monthly and yearly reports of:
Activity
LED usage and lifetime
Airflow/Pressure
Notifications of any smoke detected
Notification of any carbon monoxide.

Example 2

Alternative Design: Only have the Fins and array on one side of the filter

An alternative embodiments design comprised of arrays of UVC LEDs, rotating fins supporting each array in optimal orientation for maximum illumination and angles that encapsulates an air filter with the UVC LEDs only on the inward air flow side. This further comprises a power control module designed to regulate power to sensors and each LED element on each UVC array.

An alternative embodiments design comprised of arrays of UVC LEDs, rotating fins supporting each array in optimal orientation for maximum illumination and angles that encapsulates an air filter with the UVC LEDs only on the outward air flow side. This further comprises a power control module designed to regulate power to sensors and each LED element on each UVC array.

Example 3: Non-Rotating Fins

An alternative embodiments design comprised of arrays of UVC LEDs, stationary fins supporting each array in optimal orientation for maximum illumination and angles that encapsulates an air filter with the UVC LEDs on both sides of the filter, only on the inward air flow side, or only on the outward air flow side. This further comprises a power control module designed to regulate power to sensors and each LED element on each UVC array.

Example 4: Filter Integrated UVC LEDs

An alternative embodiments design comprised of arrays of UVC LEDs integrated with the filter with chip board, attached with adhesive, or another mechanism of directly connecting the UVC LEDs to the filter to create an integrate system. The UVC LEDs have an optimal orientation for maximum illumination and angles that encapsulates an air filter with the UVC LEDs on both sides of the filter, only on the inward air flow side, or only on the outward air flow side. This further comprises a power control module designed to regulate power to each LED element each UVC LED.

Example 5: UVC LEDs are not Connected to any Array and Optimally Distributed

An alternative embodiments design comprised of optimally placing UVC LEDs attached to rotating fins, stationary fins, or integrated with an air filter that are optimally placed to provide maximum illumination and angles that encapsulates an air filter with the UVC LEDs on both sides of the filter, only on the inward air flow side, or only on the outward air flow side. This further comprises a power control module designed to regulate power to each LED element each UVC LED.

Example 6: Power Module that has No Sensor

An alternative design of the power module only powers and regulates each LED element.

Example 7: An Alternative Design of the Power Module that Regulate Power to Each LED Element on Each UVC Array While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The invention claimed is:
1. An air filter encapsulation system for encapsulating an air filter element having an active surface, wherein in use, air passes through the air filter element to become filtered air, the air filter encapsulation system comprising:
    an air filter holder structured to hold the air filter element;
    UVC LEDs disposed on the holder, the UVC LEDs being configured to emit UVC light in the band of 100 to 280 nanometers to kill pathogens in the air at the air filter active surface;
    fins that support the UVC LEDs,
    fin angle adjusters operatively coupled to the fins, the fin angle adjusters orienting the UVC LEDs to angles that enable the UVC LEDs to encapsulate the air filter element active surface with the emitted UVC light;
    at least one sensor disposed on the air filter holder; and
    a power supply connection to supply power to the UVC LEDs.
2. The system of claim 1, wherein the air filter holder adjustably holds air filter elements of different sizes.
3. The system of claim 1 wherein the system includes a WiFi transceiver configured to be controlled with a smart device and an app to control settings and receive output signals.
4. The system of claim 1 further including a safety module connected to an electromagnetic sensor and configured to prevent exposure of UV rays to eyes or skin; and avoid risk of skin burn, the sensor automatically shutting off power to the UVC LEDs when a cover is opened.
5. The system of claim 1 wherein in order to prevent power supply overcurrent caused by over-aging UVC LEDs, the system further comprises plural sensors measuring approximated large signal resistance and small signal impedance, as indication of excess power dissipation due to degraded UVC LEDs.
6. The system of claim 1 further including a timer that indicates time to change the air filter element.
7. The system of claim 1, further comprising a Power control module designed to regulate power to sensors and each UVC LED, the power control module comprising:
    a safety shutoff feature,
    a detector to monitor airflow/rate and turn a control system ON/OFF,
    at least one sensor to monitor humidity, and
    a power regulator to regulate power level depending on detected airflow/rate.

8. The system of claim 1 wherein the fin angle adjusters rotate the fins to provide maximum UV exposure on an air intake side or air outlet side of the air filter element.

9. The system of claim 1, wherein the air filter encapsulation system comprises a safety module including:
a Sensor that detects ambient temperature,
a Sensor that detects smoke in the air, and
a Sensor that detects carbon monoxide in the air.

10. The system of claim 1, wherein the housing is adjustable to fit:
multiple standard sizes for residential air filter elements, or
multiple standard sizes for commercial air filter elements.

11. The system of claim 1 wherein, the UVC LEDs are integrated with the fins and the system uses directional positioning of the fins via the fin angle adjusters to maximize exposure of the air filter element active surface to avoid shadowing effects and to position the UVC LEDs at closest distance to the air filter element active surface.

12. The system of claim 1 wherein the fins and fin angle adjusters are configured so that placement and orientation of the UVC LEDs can be altered manually or automatically adjusted to the shape of the air filter element active surface.

13. The system of claim 1 wherein the fin placement, orientation and power design of the UVC LEDs maximizes air filter element active surface and intake and outlet with irradiance (radiant power received by surface) of 2000-8000 micro-watt/cm2.

14. The system of claim 1 wherein the UVC LEDs provide Germicidal Disinfection used to eliminate pathogens such as bacteria, mold, mildew allergens, and deactivate viruses such as SARS CoV-2.

15. The system of claim 1 wherein the fin angle adjusters are configured to rotate the fins for maximum irradiance and exposure of photons received by filter element active surface when the UVC LEDs are illuminated.

16. The system of claim 1 wherein the fin angle adjusters are configured to rotate the fins is for protection of an eye or skin of a human, and the system further comprises a protection control unit that resets power to the UVC LEDs.

17. The system of claim 1 wherein the fin angle adjusters are configured to rotate the fins for protection of an eye or skin of a human, and the system further comprises a protection control unit that resets the fin angle adjusters to provide an angle of illumination of 0°.

18. The system of claim 1 wherein the fins are oriented:
in vertical and horizontal directions facing towards side-1 of the air filter element (inward air flow), or
vertical and horizontal directions facing opposite of side-1 of the air filter element (outward air flow), or
vertical and horizontal directions facing towards side-2 of the air filter element (inward air flow), or
vertical and horizontal directions facing opposite of side-2 of the air filter element (outward air flow).

19. The system of claim 1 wherein the sensor detects rate of airflow/pressure, and the system further includes a processor coupled to the sensor that:
notifies of any current and past activities, or
notifies of running conditions, or
alerts a user of poor system performance, including detection of significant reduction in airflow and alarms a possible system maintenance or aged air filter element, or
provides periodic reports of Activity, LED usage and lifetime and/or Airflow/Pressure and/or Notifications of any smoke detected and/or Notification of any carbon monoxide.

20. A germicidal filter comprising:
a structure defining an active filtering space having an ingress side and an egress side;
an ultraviolet light array disposed on at least one of the ingress side and the egress side,
the ultraviolet light array comprising plural longitudinal strips having ultraviolet light emitting elements spaced therealong, and
fin clips disposed on the structure, the fin clips supporting and orienting the ultraviolet light array so the ultraviolet light emitting elements encapsulate the active filtering space with emitted UVC light,
wherein the ultraviolet light emitting elements provide ultraviolet light intensities of 6000 Joules/m2 for eliminating colonies of 6000-10,000 RNA viruses to enable logarithmic reduction of 1,000-10,000 colony forming units (CFUs).

21. The germicidal filter of claim 20 wherein the fin clips are configured to adjustably rotate the plural longitudinal strips relative to the active filtering space.

* * * * *